United States Patent
Nowinski

(10) Patent No.: US 8,050,475 B2
(45) Date of Patent: Nov. 1, 2011

(54) DETECTION AND LOCALIZATION OF VASCULAR OCCLUSION FROM ANGIOGRAPHY DATA

(75) Inventor: Weislaw L. Nowinski, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 452 days.

(21) Appl. No.: 12/439,084

(22) PCT Filed: Sep. 6, 2007

(86) PCT No.: PCT/SG2007/000292
§ 371 (c)(1),
(2), (4) Date: Feb. 26, 2009

(87) PCT Pub. No.: WO2008/030192
PCT Pub. Date: Mar. 13, 2008

(65) Prior Publication Data
US 2009/0324052 A1    Dec. 31, 2009

Related U.S. Application Data

(60) Provisional application No. 60/842,377, filed on Sep. 6, 2006.

(51) Int. Cl.
*G06K 9/00* (2006.01)
(52) U.S. Cl. .......................... 382/130; 382/128; 128/922
(58) Field of Classification Search .......... 328/128–134; 128/920, 922
See application file for complete search history.

(56) References Cited

U.S. PATENT DOCUMENTS 7,783,132 B2 *   8/2010   Nowinski et al. ............. 382/294
2004/0106864 A1  6/2004   Rose et al.

FOREIGN PATENT DOCUMENTS

WO    0156466      8/2001
WO    02065913     8/2002

OTHER PUBLICATIONS

International Search Report PCT/SG2007/00292; Dated Nov. 17, 2007.
Wieslaw L. Nowinski, et al, "Analysis of Ischemic Stroke MR Images by Means of Brain Atlases of Anatomy and Blood Supply Territories", Academic Radiology, vol. 13, No. 8, pp. 1025-1034, Aug. 2006.
Wieslaw L. Nowinski, et al, "Three-dimensional Atlas of the Brain Anatomy and Vasculature", Informatics in Radiology (infoRAD), vol. 25, No. 1, pp. 263-271, Jan.-Feb. 2005.

\* cited by examiner

*Primary Examiner* — David Mis
(74) *Attorney, Agent, or Firm* — Cantor Colburn LLP

(57) ABSTRACT

A technique for detecting and localizing vascular occlusions in the brain of a patient is presented. The technique uses volumetric angiographic data of the brain. A mid-sagittal plane and/or lines is/are identified within the set of angiographic data. Optionally, the asymmetry of the hemispheres is measured, thereby obtaining an initial indication of whether an occlusion might be present. The angiographic data is mapped to pre-existing atlas of blood supply territories, thereby obtaining the portion of the angiographic data corresponding to each of the blood supply territories. For each territory (including any sub-territories), the asymmetry of the corresponding portion of the angiographic data about the mid-sagittal plane/lines is measured, thereby detecting any of the blood supply territory including an occlusion. The angiographic data for any such territory is displayed by a three-dimensional imaging technique.

16 Claims, 2 Drawing Sheets

DETECTION AND LOCALIZATION OF VASCULAR OCCLUSION FROM ANGIOGRAPHY DATA

FIELD OF THE INVENTION

The present invention relates to methods and computer systems for detecting whether a patient suffers from an occluded blood vessel, and in the case that occlusion is detected, to localization of the occlusion.

BACKGROUND OF THE INVENTION

Determination whether a blood vessel is occluded (i.e. blocked) or patent (i.e. open), and, in the case of an occlusion being identified, localization of this occlusion, are important in the diagnosis and treatment of vascular diseases. This is also critical in acute stroke management. Imaging is a means to obtain this information. Volumetric angiographic data (that is, a set of data in which elements of the data correspond to respective points within a three-dimensional region) can be acquired with various imaging techniques, such as magnetic resonance angiography (MRA), computed tomography angiography (CTA) or X-ray rotation angiography. Present techniques for detecting occlusions involve a requirement to segment volumetric angiographic images (i.e. partition the images into regions which are the estimates of the positions of cerebral structures within the image). For this purpose, the Marching Cubes algorithm is typically used. The whole procedure of iso-surface segmentation and surface display is time consuming, particularly, in acute stroke management. Alternatively, the scan can be examined by using Maximum Intensity Projection (MIP) display. MIP, as a 2D projection of a 3D volume does not contain full information.

SUMMARY OF THE INVENTION

The present invention aims to provide a new and useful method to detect and localize an occlusion, and computer systems for implementing the method.

In general terms, the invention proposes detecting occlusions by an asymmetry measurement of a set of angiographic data around the mid-sagittal plane (MSP) of a brain. Alternatively, particularly if the inter-hemispheric fissure is curved, instead of using the MSP, it may be better to obtain a different mid-sagittal line for each slice, and detect occlusions by determining the asymmetry around these lines. In other words, in both these techniques at least one mid-sagittal position is found, and the occlusion detected by determining the asymmetry about these position(s).

A first specific expression of the invention is a method for detecting a vascular occlusion from a set of angiographic data relating to the brain of a patient, the method including:
(i) locating the mid-sagittal plane within the set of angiographic data;
(ii) mapping the angiographic data to a pre-existing atlas of blood supply territories, thereby obtaining the portion of the angiographic data corresponding to each of one or more blood supply territories;
(iii) for each of the blood supply territories, evaluating the asymmetry of the corresponding portion of the angiographic data about the identified mid-sagittal plane; and
(iv) according to the evaluated asymmetry of the portion of the angiographic data corresponding to each blood supply territory, detecting the presence of an occlusion in any of the blood supply territories.

An alternative expression of this same concept, in the case that midsagittal lines are used instead of a single MSP, is a method for detecting a vascular occlusion from a set of angiographic data relating to the brain of a patient, the method including:
(i) for each of a plurality of slices of the angiographic data, locating respective mid-sagittal lines;
(ii) mapping the angiographic data to a pre-existing atlas of blood supply territories, thereby obtaining the portion of the angiographic data corresponding to each of one or more blood supply territories;
(iii) for each of the blood supply territories, evaluating the asymmetry of the corresponding portion of the angiographic. data within each slice about the corresponding identified mid-sagittal lines; and
(iv) according to the evaluated asymmetry of the portion of the angiographic data corresponding to each blood supply territory, detecting the presence of an occlusion in any of the blood supply territories.

In either case, step (ii) may also include obtaining the portion of the angiographic data corresponding to one or more blood supply sub-territories. In this case, in step (iii), the asymmetry may be evaluated for each of the sub-territories, and in step (iv) the presence of an occlusion may be identified in any of the sub-territories.

Preferred embodiments of the invention make it possible to detect and localise an occlusion without segmentation of the vascular data. This processing is much faster than the extraction of iso-surface and displaying it by means of the Marching Cubes, which is critical in stroke management. In addition, this detection can be done automatically without the operator intervention, which allows for its application in computer-aided diagnosis and decision support systems.

Note that the present approach is based on ROL, with the regions of interest based on the blood territories (and sub-territories). Step (i) precedes step (ii).

The invention further proposes that once an occlusion is detected in a portion of the angiographic data corresponding to a blood territory, that portion of the angiographic data is displayed by a three-dimensional imaging technique. This may be performed by projecting the portion of the angiographic data onto planes, for example onto coronal, axial or sagittal planes.

Embodiments of the method may use a pre-existing atlas of blood supply territories, as well as existing algorithms for calculation of the midsagittal plane (MSP), for asymmetry quantification, and mapping the atlas of blood supply territories to the angiographic data.

The automatic detection and localisation process may be implemented, for example, in an automated CAD system for use in stroke diagnosis, predication and treatment. Note that all steps of the method may be performed computationally, with substantially no operator involvement. The invention is expressed above as a method, but may alternatively be expressed as a computer system which performs the method, or as software which can be run by a computer system to perform the method.

BRIEF DESCRIPTION OF THE DRAWINGS

An embodiment of the invention will now be described for the sake of example only with reference to the following figures, in which.

DETAILED DESCRIPTION OF THE EMBODIMENT

Figure 1:
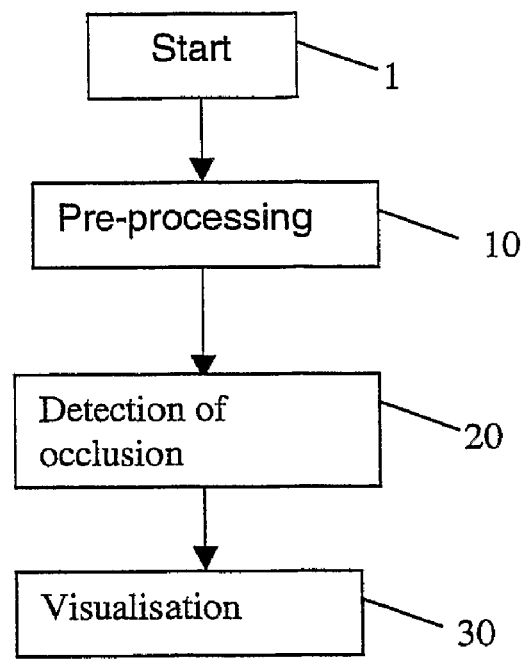
FIG. 1 is a flow diagram of the main steps of the embodiment.
Figure 2:
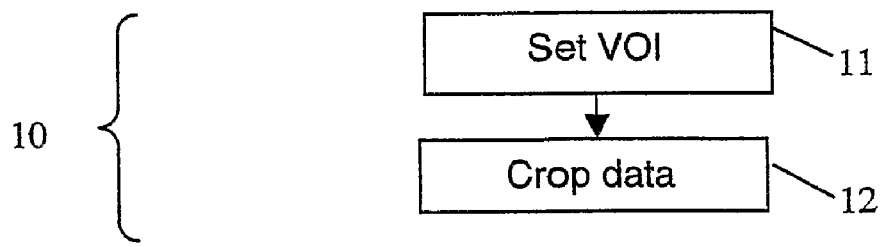
FIG. 2 is a diagram of the sub-steps of a pre-processing step of the embodiment of FIG. 1.

An embodiment of the invention will now be described with reference to FIG. 1. The embodiment takes as its input, at step 1, a set of three-dimensional volumetric angiographic data, which has been acquired with any suitable imaging technique, such as magnetic resonance angiography (MRA), computed tomography angiography (CTA) or X-ray rotation angiography In step 10, the method pre-processes the volumetric angiographic data prior to their analysis and visualization. The sub-steps of the pre-processing step 10 are shown in FIG. 2.

The volumetric angiographic data typically depicts not only the vessels but also other structures including scalp, skull, muscles, fat, and some other bones. To facilitate analysis, some unnecessary structures are eliminated by setting a suitable volume of interest (VOI) (sub-step 11), and removing the voxels outside this volume ("cropping"—sub-step 12). The VOI can be set in several ways, depending on the specific application. In particular, the VOI setting and data cropping can be done as follows:

1. Generate axial, coronal, and sagittal sections from the volumetric angiographic data by orthogonal reformatting.
2. Select the range of the axial sections and set an ellipse to encompass the brain.
3. Propagate this ellipse across all axial slices within the selected range.
4. Crop the volume by removing the voxels located outside the ellipses.
5. For the resulting VOI, repeat the steps 2-4 for the coronal and sagittal orientations (thus, the pair of sub-steps 11 and 12 of FIG. 2 are performed three times in total), resulting in the final VOI.

Analysis (Step 20)

For the VOI which is the output of step 10, the mid-sagittal plane (MSP) is calculated first (sub-step 21). It can be computed by using any existing algorithms, in particular one of our previous algorithms [1], [2]. Alternatively, the technique can be further improved slice-wise by calculating a midsagittal line for every slice. The MSP may be the starting location for this calculation.

Vessel occlusion causes the lack of blood flow which results in lateral asymmetry with respect to the MSP. To localize the occlusion, this asymmetry study should be constrained to a given blood supply territory (BST), or sub-territory. The BSTs (or sub-territories) are determined in the angiography volume by means of our BST atlas [5]. In sub-step 22, the BST atlas is superimposed on the angiography data by using any method; in particular our FTT [6] can be used. Then, asymmetry is identified (sub-step 23). In sub-step 23 one of several methods can be exploited to measure this asymmetry, in particular one of our previous methods [3], [4], [0]. If a different MS line is found for each slice, the same asymmetry test (or tests) is performed for each slice, but the brain is divided differently into the hemispheres. To determine whether there is an occlusion in a given territory, it is possible to study the whole volume to detect an occlusion; and then do the same for each slice (this can enhance the occlusion detection and localize the occlusion more accurately.

The detailed steps are as follows:
1. Calculate the MSP (sub-step 21).
2. Superimpose the BST atlas (sub-step 22).
3. Quantify the left-right hemisphere asymmetry within the anterior cerebral artery (ACA), including its penetrating and terminal branches. If necessary, the ACA territory can be further subdivided into sub-territories.
4. Quantify the left-right hemisphere asymmetry within the middle cerebral artery (MCA), including its penetrating and terminal branches. If necessary, the MCA territory can be further subdivided into sub-territories.
5. Quantify the left-right hemisphere asymmetry within the posterior cerebral artery (PCA), including its penetrating and terminal branches. If necessary, the PCA territory can be further subdivided into sub-territories.

Figure 3:
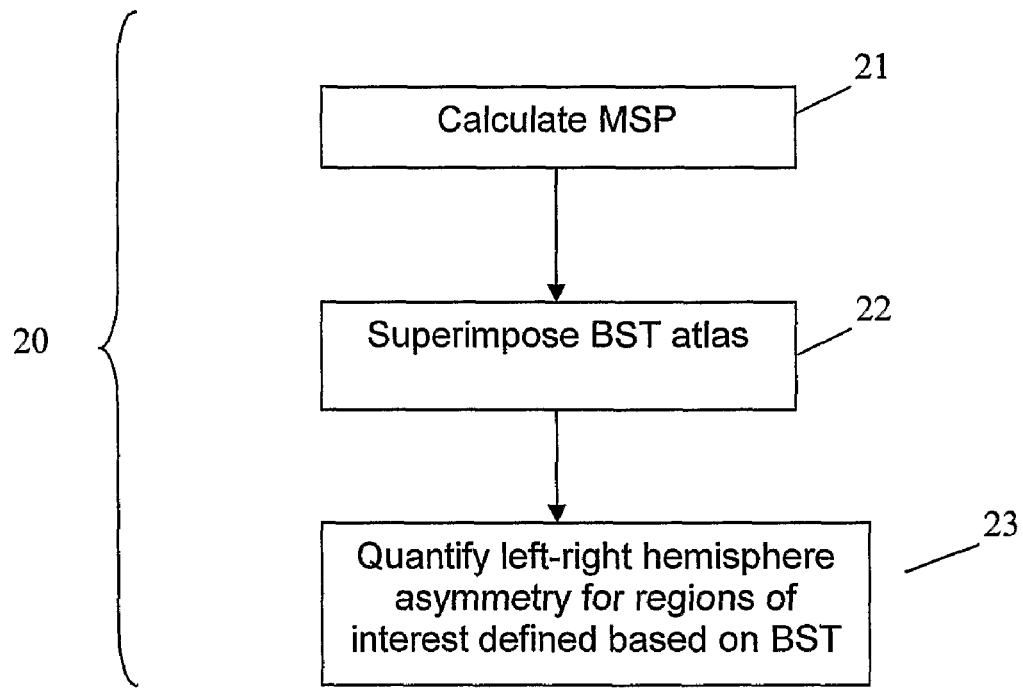
FIG. 3 is a diagram of the sub-steps of an analysis step of the embodiment of FIG. 1.
Figure 4:
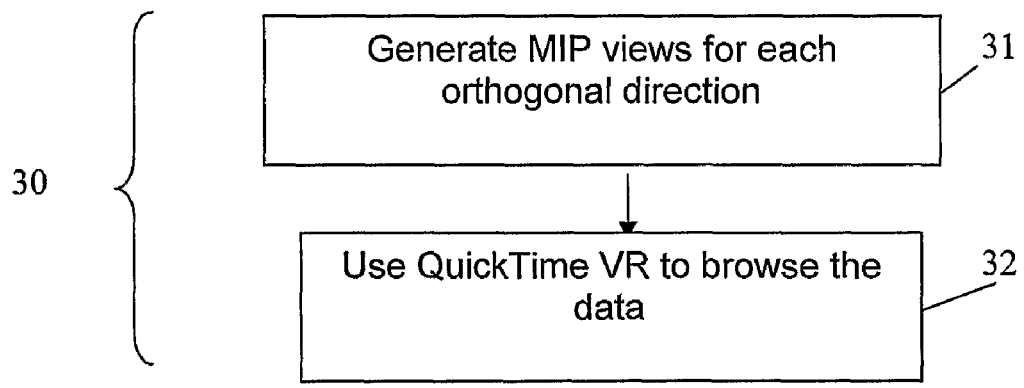
FIG. 4 is a diagram of the sub-steps of an imaging step of the embodiment of FIG. 1.

Steps 4 to 6 of this list are shown collectively as sub-step 23 in FIG. 3.

Visualization (Step 30)

An optional visualization step may then be performed, e.g. when desired by a human operator. Visualization proposed here allows exploration of the angiography data in three dimensions without segmenting them. It uses the maximum intensity projection (MIP) technique to generate MIP views (sub-step 31), followed by a Quick Time Virtual Reality (QTVR) approach [7] to view the MIP views (sub-step 32). The MSP views can be generated in any direction with an arbitrary step. In particular, the detailed steps may be the following:

1. Generate the MIP views with a small angular step around the axis perpendicular to the axial direction.
2. Generate the MIP views with a small angular step along the axis perpendicular to the coronal direction.
3. Generate the MIP views with a small angular step along the axis perpendicular to the sagittal direction.
4. Use the QT VR to browse the MIP views in three-dimensions.

Steps 1 to 3 correspond collectively to sub-step 31 in FIG. 5, and step 4 corresponds to sub-step 32.

Although only a single embodiment of the invention has been described in detail, many variations may be made within the scope of the invention as defined in the claims as will be clear to a skilled reader. For example, the order of the steps need not be exactly as given above.

REFERENCES

1. Hu Q, Nowinski W L: Method and apparatus for determining symmetry in 2D and 3D images, international application number PCT/SG02/00006, 18 Jan. 2002; published international application no: WO03/060827
2. Bhanu Prakash K N, Volkov I, Nowinski W L: Locating a mid-sagittal plane, BIL/P//1666/US filed on 2 Apr. 2004. BIL/P/1666/2475/PCT. PCT/SG2005/000106 application filed on 1 Apr. 2005. WO 2005/096227 A1 published on 13 Oct. 2005. SG200604563-7 filed on 6 Jun. 2006 (former invention title: Extraction of mid-sagittal plane from MR brain volume—Entropy and energy based approaches).
3. Volkau I, Nowinski W L: A method and apparatus for determining asymmetry in an image, BIL//P/1833/SG, SG 200405043-1 filed on 10 Sep. 2004. BIL/P/1833/2837/PCT-PCT/SG2005/000302 filed on 1 Sep. 2005. WO2006/028416 published on 16 Mar. 2006. (former invention title: Information based method for identification and localization of pathology in MRI Neuroimages)
4. Nowinski W L, Hu Q: Method and apparatus for identifying pathology in brain images, BIL/P//1226/PCT, PCT/

5. Nowinski W L, Qian G, Bhanu Prakash K N, Thirunavuukarasuu A, Hu Q M, Ivanov N, Parimal A S, Runge V L, Beauchamp N J: Analysis of ischemic stroke MR images by means of brain atlases of anatomy and blood supply territories. Academic Radiology 2006; 13(8):1025-1034.
6. Nowinski W L, Qian G, Bhanu Prakash K N, Hu Q, Aziz A: Fast Talairach Transformation for magnetic resonance neuroimages. Journal of Computer Assisted Tomography 2006; 30(4):629-41.
7. Apple's QuickTime VR software: http://www.apple.com/quicktime/resources/tools/qtvr.html
8. Gupta V, Bhanu Prakash K N, Nowinski W L: *Automatic identification of infarct slices and hemisphere from DWI scans*. BIL/P/04489/00/US, U.S. 60/273,019 Provisional application filed on 6 Dec. 2006.
9. W. Lorensen and H. Cline, "Marching Cubes: A high resolution 3-D surface construction algorithm", *Proc. SIGGRAPH '98*, in *Computer Graphics*, vol. 21, no. 4, July 1987.

The invention claimed is:

1. A method for detecting a vascular occlusion from a set of angiographic data relating to the brain of a patient, the method including:
    (i) locating the mid-sagittal plane within the set of angiographic data;
    (ii) mapping the angiographic data to a pre-existing atlas of blood supply territories, thereby obtaining the portion of the angiographic data corresponding to each of one or more blood supply territories;
    (iii) for each of the blood supply territories, evaluating the asymmetry of the corresponding portion of the angiographic data about the identified mid-sagittal plane; and
    (iv) according to the evaluated asymmetry of the portion of the angiographic data corresponding to each blood supply territory, detecting the presence of an occlusion in any of the blood supply territories.

2. A method according to claim 1 in which step (ii) includes obtaining the portion of the angiographic data corresponding to one or more blood supply sub-territories; in step (iii), the asymmetry is evaluated for each of the sub-territories; and in step (iv) the presence of an occlusion is identified in any of the sub territories.

3. A method according to claim 1 including a pre-processing step of cropping the angiographic data to remove a part of the angiographic data which relates to locations outside the brain of the patient.

4. A method according to claim 1 which, upon the detection of an occlusion within any of the blood supply territories, the portion of the angiographic data corresponding to that blood supply territory is displayed by a three-dimensional imaging technique.

5. A method according to claim 4 in which the three-dimensional imaging technique includes obtaining and displaying projections of the corresponding portion of angiographic data onto one or more planes.

6. A computer program product comprising software which, upon being run by a computer system, causes the computer system to detect a vascular occlusion from a set of angiographic data relating to the brain of a patient, by performing a method according to claim 1.

7. A method for detecting a vascular occlusion from a set of angiographic data relating to the brain of a patient, the method including:
    (i) for each of a plurality of slices of the angiographic data, locating respective mid-sagittal lines;
    (ii) mapping the angiographic data to a pre-existing atlas of blood supply territories, thereby obtaining the portion of the angiographic data corresponding to each of one or more blood supply territories;
    (iii) for each of the blood supply territories, evaluating the asymmetry of the corresponding portion of the angiographic data within each slice about the corresponding identified mid-sagittal lines; and
    (iv) according to the evaluated asymmetry of the portion of the angiographic data corresponding to each blood supply territory, detecting the presence of an occlusion in any of the blood supply territories.

8. A method according to claim 7 in which step (ii) includes obtaining the portion of the angiographic data corresponding to one or more blood supply sub-territories; in step (iii), the asymmetry is evaluated for each of the sub-territories; and in step (iv) the presence of an occlusion is identified in any of the sub territories.

9. A method according to claim 7 including a pre-processing step of cropping the angiographic data to remove a part of the angiographic data which relates to locations outside the brain of the patient.

10. A method according to claim 7 which, upon the detection of an occlusion within any of the blood supply territories, the portion of the angiographic data corresponding to that blood supply territory is displayed by a three-dimensional imaging technique.

11. A method according to claim 10 in which the three-dimensional imaging technique includes obtaining and displaying projections of the corresponding portion of angiographic data onto one or more planes.

12. A computer program product comprising software which, upon being run by a computer system, causes the computer system to detect a vascular occlusion from a set of angiographic data relating to the brain of a patient, by performing a method according to claim 7.

13. A computer system for detecting a vascular occlusion from a set of angiographic data relating to the brain of a patient, the computer system including a processor arranged to:
    (i) locate the mid-sagittal plane within the set of angiographic data;
    (ii) map the angiographic data to a pre-existing atlas of blood supply territories, thereby obtaining the portion of the angiographic data corresponding to each of one or more blood supply territories;
    (iii) for each of the blood supply territories, evaluate the asymmetry of the corresponding portion of the angiographic data about the identified mid-sagittal plane; and
    (iv) according to the evaluated asymmetry of the portion of the angiographic data corresponding to each blood supply territory, output a signal indicative of the presence of an occlusion in any of the blood supply territories.

14. A computer system according to claim 13 further having a display unit for displaying images representative of the portion of the angiographic data corresponding to each blood supply territory for which the presence of an occlusion is indicated by said output signal.

15. A computer system for detecting a vascular occlusion from a set of angiographic data relating to the brain of a patient, the computer system including a processor arranged to:
    (i) locate, for each of a plurality of slices of the angiographic data, respective mid-sagittal lines;

(ii) map the angiographic data to a pre-existing atlas of blood supply territories, thereby obtaining the portion of the angiographic data corresponding to each of one or more blood supply territories;
(iii) for each of the blood supply territories, evaluate the asymmetry of the corresponding portion of the angiographic data within each slice about the corresponding identified mid-sagittal lines; and
(iv) according to the evaluated asymmetry of the portion of the angiographic data corresponding to each blood supply territory, output a signal indicative of the presence of an occlusion in any of the blood supply territories.

16. A computer system according to claim 15 further having a display unit for displaying images representative of the portion of the angiographic data corresponding to each blood supply territory for which the presence of an occlusion is indicated by said output signal.

* * * * *

UNITED STATES PATENT AND TRADEMARK OFFICE
CERTIFICATE OF CORRECTION

| | | |
|---|---|---|
| PATENT NO. | : 8,050,475 B2 | Page 1 of 1 |
| APPLICATION NO. | : 12/439084 | |
| DATED | : November 1, 2011 | |
| INVENTOR(S) | : Wieslaw L. Nowinski | |

It is certified that error appears in the above-identified patent and that said Letters Patent is hereby corrected as shown below:

On the Title page, at item (75), the inventor's name should read: Wieslaw L. Nowinski Signed and Sealed this Thirteenth Day of March, 2012

David J. Kappos
*Director of the United States Patent and Trademark Office*